US009615933B2

United States Patent
Frasier et al.

(10) Patent No.: US 9,615,933 B2
(45) Date of Patent: Apr. 11, 2017

(54) EXPANDABLE RING INTERVERTEBRAL FUSION DEVICE

(75) Inventors: William Frasier, New Bedford, MA (US); Narendren Renganathan, Burlington, MA (US); Glen Presbrey, Mapleville, RI (US); Michael A Fisher, Middleboro, MA (US); John Riley Hawkins, Cumberland, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 840 days.

(21) Appl. No.: 12/559,537

(22) Filed: Sep. 15, 2009

(65) Prior Publication Data

US 2011/0066192 A1    Mar. 17, 2011

(51) Int. Cl.
*A61F 2/44* (2006.01)
*A61F 2/28* (2006.01)
*A61F 2/30* (2006.01)

(52) U.S. Cl.
CPC ............ *A61F 2/441* (2013.01); *A61F 2/4465* (2013.01); *A61F 2002/2817* (2013.01); *A61F 2002/3052* (2013.01); *A61F 2002/30062* (2013.01); *A61F 2002/30092* (2013.01); *A61F 2002/30131* (2013.01); *A61F 2002/30224* (2013.01); *A61F 2002/30289* (2013.01); *A61F 2002/30291* (2013.01); *A61F 2002/30476* (2013.01); *A61F 2002/30579* (2013.01); *A61F 2002/30583* (2013.01); *A61F 2002/30596* (2013.01); *A61F 2002/30601* (2013.01); *A61F 2002/30672* (2013.01); *A61F 2002/30677* (2013.01);

(Continued)

(58) Field of Classification Search
USPC ............... 606/246–249; 623/17.11–17.16, 623/1.11–1.12, 1.15–1.18, 1.2
See application file for complete search history.

(56) References Cited

U.S. PATENT DOCUMENTS 2,677,369 A   5/1954   Knowles
3,875,595 A   4/1975   Froning
(Continued)

FOREIGN PATENT DOCUMENTS

EP   1575457   5/2008
EP   1575459   5/2008
(Continued)

OTHER PUBLICATIONS

Allcock, Polyphosphazenes, *The Encyclopedia of Polymer Science*, 1998, pp. 31-41, vol. 13, Wiley Intersciences, John Wiley & Sons.
(Continued)

*Primary Examiner* — Nicholas Woodall (57) ABSTRACT

An expandable tube having a substantially semicircular unexpanded shape is inserted into the disc space after the disc material has been removed therefrom. A plurality of expandable lockable rings are passed over this tube in their unexpanded states and positioned along the anterior edge of the endplates. The tube is then expanded, thereby forcing the rings to expand. The rings hold their final expanded configuration via a one-way locking mechanism. Once sufficient distraction is achieved and the rings locked, the tube is collapsed and removed, thereby leaving the expanded, locked rings behind to support the disc space.

5 Claims, 10 Drawing Sheets

(52) U.S. Cl.
CPC ............... *A61F 2002/4415* (2013.01); *A61F 2210/0004* (2013.01); *A61F 2210/0014* (2013.01); *A61F 2210/0085* (2013.01); *A61F 2220/0025* (2013.01); *A61F 2230/0013* (2013.01); *A61F 2230/0069* (2013.01); *A61F 2230/0091* (2013.01); *A61F 2250/0059* (2013.01)

(56) References Cited

U.S. PATENT DOCUMENTS

| | | | |
|---|---|---|---|
| 4,105,034 A | 8/1978 | Shalaby | |
| 4,130,639 A | 12/1978 | Shalaby | |
| 4,140,678 A | 2/1979 | Shalaby | |
| 4,141,087 A | 2/1979 | Shalaby | |
| 4,205,399 A | 6/1980 | Shalaby | |
| 4,208,511 A | 6/1980 | Shalaby | |
| 5,167,614 A * | 12/1992 | Tessmann et al. | 623/1.15 |
| 5,344,444 A | 9/1994 | Glastra | |
| 5,441,515 A * | 8/1995 | Khosravi et al. | 606/194 |
| 5,443,514 A | 8/1995 | Steffee | |
| 5,464,929 A | 11/1995 | Bezwada | |
| 5,595,751 A | 1/1997 | Bezwada | |
| 5,597,579 A | 1/1997 | Bezwada | |
| 5,607,687 A | 3/1997 | Bezwada | |
| 5,618,552 A | 4/1997 | Bezwada | |
| 5,620,698 A | 4/1997 | Bezwada | |
| 5,645,850 A | 7/1997 | Bezwada | |
| 5,648,088 A | 7/1997 | Bezwada | |
| 5,658,336 A | 8/1997 | Pisharodi | |
| 5,698,213 A | 12/1997 | Jamiolkowski | |
| 5,700,583 A | 12/1997 | Jamiolkowski | |
| 5,716,415 A | 2/1998 | Steffee | |
| 5,824,054 A * | 10/1998 | Khosravi | A61F 2/92 606/191 |
| 5,836,948 A | 11/1998 | Zucherman | |
| 5,859,150 A | 1/1999 | Jamiolkowski | |
| 6,049,026 A | 4/2000 | Muschler | |
| 6,086,613 A | 7/2000 | Camino et al. | |
| 6,264,695 B1 | 7/2001 | Stoy | |
| 6,309,421 B1 | 10/2001 | Pisharodi | |
| 6,332,894 B1 | 12/2001 | Stalcup | |
| 6,425,915 B1 * | 7/2002 | Khosravi et al. | 623/1.22 |
| 6,582,467 B1 | 6/2003 | Teitelbaum | |
| 6,632,235 B2 | 10/2003 | Weikel | |
| 6,656,178 B1 | 12/2003 | Veldhuizen | |
| 6,706,069 B2 | 3/2004 | Berger | |
| 6,706,070 B1 | 3/2004 | Wagner | |
| 6,746,475 B1 * | 6/2004 | Rivelli, Jr. | 623/1.15 |
| 6,932,843 B2 | 8/2005 | Smith | |
| 6,942,698 B1 | 9/2005 | Jackson | |
| 6,962,606 B2 | 11/2005 | Michelson | |
| 6,981,975 B2 | 1/2006 | Michelson | |
| 6,981,981 B2 | 1/2006 | Reiley | |
| 7,094,257 B2 | 8/2006 | Mujwid | |
| 7,789,898 B2 | 9/2010 | Peterman | |
| 7,803,162 B2 | 9/2010 | Marnay | |
| 8,029,512 B2 | 10/2011 | Paltzer | |
| 8,097,037 B2 | 1/2012 | Serhan | |
| 8,167,915 B2 | 5/2012 | Ferree | |
| 8,257,436 B2 | 9/2012 | Jackson | |
| 8,403,988 B2 | 3/2013 | Frasier | |
| 8,685,097 B2 | 4/2014 | Frasier | |
| 2001/0010633 A1 | 8/2001 | Apfelbeck | |
| 2001/0032020 A1 | 10/2001 | Besselink | |
| 2002/0058947 A1 | 5/2002 | Hochschuler | |
| 2002/0082598 A1 | 6/2002 | Teitelbaum | |
| 2002/0156531 A1 | 10/2002 | Felt | |
| 2002/0198526 A1 | 12/2002 | Shaolian | |
| 2003/0028251 A1 | 2/2003 | Mathews | |
| 2003/0208203 A1 | 11/2003 | Lim | |
| 2004/0006341 A1 | 1/2004 | Shaolian | |
| 2004/0022672 A1 | 2/2004 | Castellini | |
| 2004/0073213 A1 | 4/2004 | Serhan | |
| 2004/0215193 A1 | 10/2004 | Shaolian | |
| 2004/0230309 A1 | 11/2004 | DiMauro | |
| 2005/0177235 A1 | 8/2005 | Baynham | |
| 2005/0209696 A1 | 9/2005 | Lin | |
| 2005/0209697 A1 | 9/2005 | Paponneau | |
| 2005/0209698 A1 | 9/2005 | Gordon | |
| 2005/0251260 A1 | 11/2005 | Gerber | |
| 2005/0251262 A1 | 11/2005 | De Villiers | |
| 2005/0256576 A1 | 11/2005 | Moskowitz | |
| 2005/0256577 A1 | 11/2005 | Baumgartner | |
| 2006/0004326 A1 | 1/2006 | Collins | |
| 2006/0004458 A1 | 1/2006 | Collins | |
| 2006/0030926 A1 * | 2/2006 | Berra | 623/1.13 |
| 2006/0247634 A1 | 11/2006 | Warner | |
| 2007/0149978 A1 | 6/2007 | Shezifi | |
| 2007/0233254 A1 | 10/2007 | Grotz | |
| 2008/0109082 A1 | 5/2008 | Fink | |
| 2009/0005870 A1 | 1/2009 | Hawkins | |
| 2010/0010633 A1 | 1/2010 | Kohm | |
| 2011/0066244 A1 | 3/2011 | Frasier | |
| 2013/0178941 A1 | 7/2013 | Frasier et al. | |
| 2014/0163686 A1 | 6/2014 | Frasier | |

FOREIGN PATENT DOCUMENTS

| | | |
|---|---|---|
| EP | 1575458 | 2/2009 |
| EP | 1536808 | 7/2009 |
| WO | WO 03007853 | 1/2003 |
| WO | WO 2004073562 | 9/2004 |

OTHER PUBLICATIONS

Cohn, Polymer Preprints (ACS Division of Polymer Chemistry), 1989, p. 498, vol. 30(1).

Heller, Poly(Ortho Esters), *Handbook of Biodegradable Polymers*, edited by Domb, et al, 1997, pp. 99-118, Hardwood Academic Press.

Kemnitzer and Kohn, Degradable Polymers Derived From the Amin Acod L-Tyrosine, *Handbook of Biodegradable Polymers*, edited by Domb, et. al., 1997, pp. 251-272, Hardwood Academic Press.

Vandorpe, Biodegradable Polyphosphazenes for Biomedical Applications, *Handbook of Biodegradable Polymers*, edited by Domb, et al, 1997, pp. 161-182, Hardwood Academic.

* cited by examiner

EXPANDABLE RING INTERVERTEBRAL FUSION DEVICE

BACKGROUND OF THE INVENTION

The natural intervertebral disc contains a jelly-like nucleus pulposus surrounded by a fibrous annulus fibrosus. Under a physiologic axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1β and TNF-α as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, which changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices" or "fusion cages".

Current interbody fusion techniques typically include not only an interbody fusion cage, but also supplemental fixation hardware such as fixation screws. This hardware adds to the time, cost, and complexity of the procedure. It also can result in tissue irritation when the cage's profile extends out of the disc space, thereby causing dysphonia/dysphagia in the cervical spine and vessel erosion in the lumbar spine. In addition, the fixation hardware typically includes a secondary locking feature, which adds to the bulkiness of the implant and time required for the procedure. Furthermore, existing fixation hardware may prevent the implantation of additional hardware at an adjacent location, and so may require removal and potentially extensive revision of a previous procedure.

SUMMARY OF THE INVENTION

In accordance with one embodiment of the present invention, an expandable tube having a substantially semicircular unexpanded shape is inserted into the disc space after the disc material has been removed therefrom. A plurality of expandable lockable rings are passed over this tube in their unexpanded states and positioned along the anterior edge of the vertebral endplates. The tube is then expanded, thereby forcing the rings to expand. The rings hold their final expanded configuration via a one-way locking mechanism. Once sufficient distraction is achieved and the rings are locked, the tube is collapsed and removed, thereby leaving the expanded, locked rings behind to support the disc space and facilitate fusion.

Therefore, in accordance with the present invention, there is provided an assembly for inserting an intervertebral fusion device, comprising:
  a) a first flexible tube having an outer radius and a throughbore, a first unexpanded state and a second expanded state,
  b) a plurality of rings having a first unexpanded state and a second expanded, locked state,
  wherein each ring surrounds the outer radius of the tube,
  wherein the plurality of rings are in their unexpanded states when the tube is initially in its unexpanded state, and
  wherein the plurality of rings are in their locked expanded states once the tube has been placed in its expanded state.

In a second embodiment, an assembly (in which the rings are provided on the tube) is inserted into the disc space.

Therefore, in accordance with the present invention, there is provided a method of distracting a disc space having opposed vertebral endplates, comprising the steps of:
  a) inserting a tube into the disc space, the tube carrying a plurality of rings thereon, wherein the rings are in a first unexpanded state and have a one-way locking mechanism,
  b) positioning the rings along an anterior edge of the endplates,
  c) expanding the tube to force the rings to expand and lock,
  d) collapsing the expanded tube to leave the rings behind to support the disc space, and
  e) removing the tube.

DETAILED DESCRIPTION OF THE INVENTION

Figure 1A:
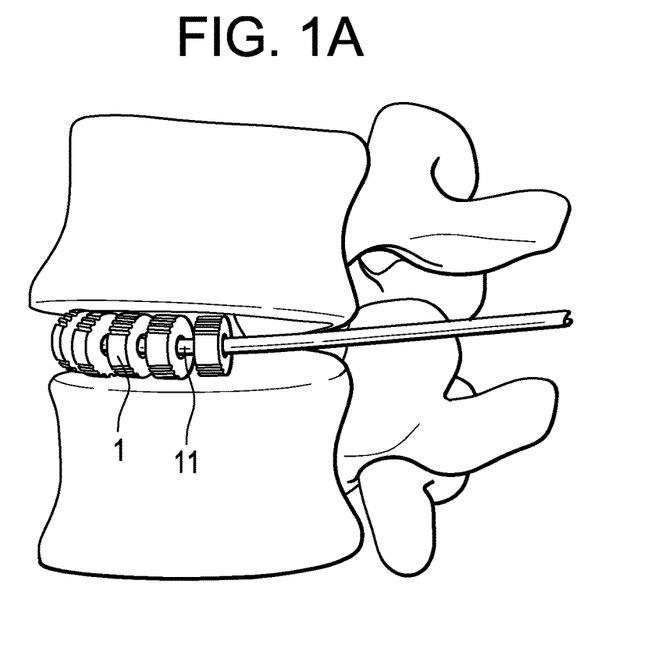
FIG. 1a discloses a ring of the present invention in its unexpanded (collapsed) state.
Figure 1B:
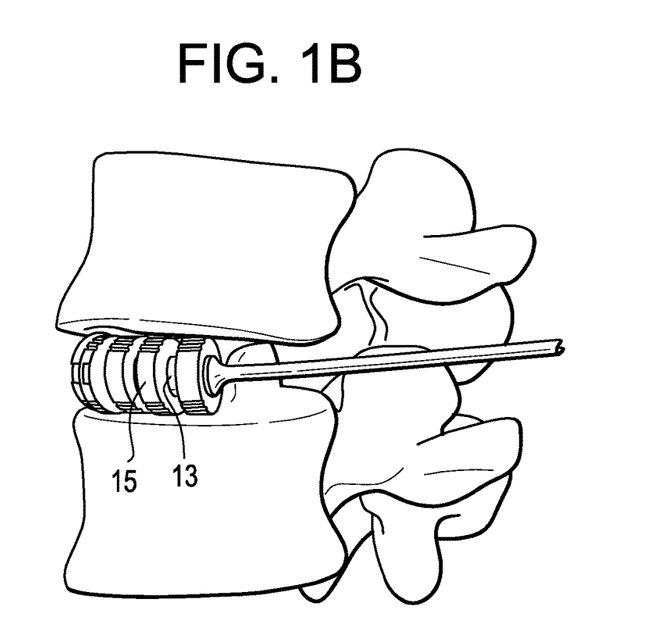
FIG. 1b discloses a ring of FIG. 1a in its fully expanded, locked state.
Figure 2A:
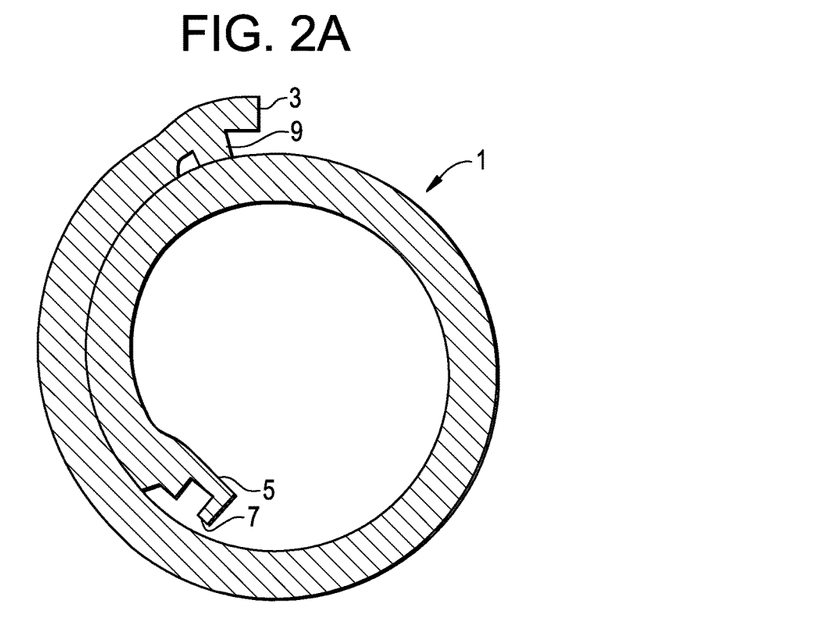
FIG. 2a discloses a collapsed ring-balloon assembly of the present invention inserted into a disc space.
Figure 2B:
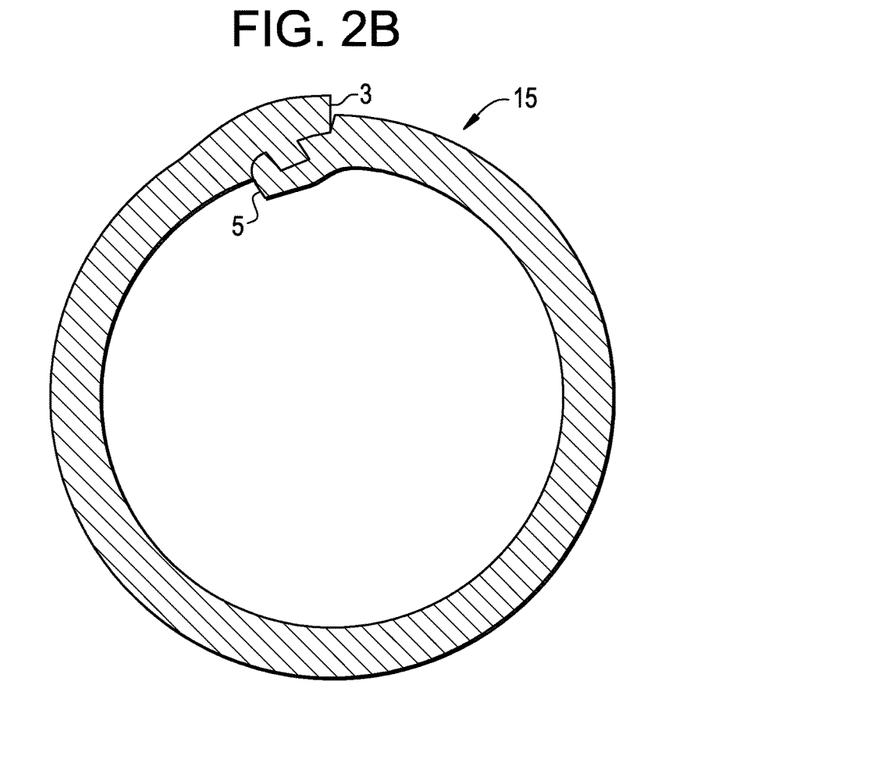
FIG. 2b discloses an expanded, locked ring-balloon assembly of FIG. 2a supporting the disc space.

FIGS. 1a and 2a represent the rings of the present invention when the balloon 11 is in its collapsed state. In these embodiments, the ring 1 is open, has a spiral shape, and each of the outer end 3 and the inner end 5 of the spiral has a mating tooth 7, 9. In its FIGS. 1a and 2a collapsed configuration, the coil is in a fairly tight shape and so possesses a small profile. In addition, the two mating teeth 7, 9 are not in contact with one another. Now referring to FIGS. 1b and 2b, as the balloon 13 finishes its expansion to achieve its expanded state, the ring 15 likewise finishes its expansion as well, and the mating tooth 7 associated with the inner end 5 of the expanded spiral bears against the mating tooth 9 associated with the outer end 3 of the ring. Because the mating teeth 7, 9 have an interlocking design, the expanded spiral may not return to the FIGS. 1a/2a collapsed configuration. At this point, the spiral is in its fully expanded, locked configuration and the semicircular plurality of such spirals form a load-bearing construct capable of facilitating fusion. Because the rings are now in a load-bearing, self-supporting configuration, the balloon may now be deflated and removed from the disc space.

Therefore, in accordance with the present invention, there is provided a method of distracting a disc space having opposing vertebral endplates, comprising the steps of:
a) inserting a tube having a throughbore into the disc space,
b) passing a plurality of rings having a one-way locking mechanism over the tube in a first unexpanded state,
c) positioning the plurality of rings along an anterior edge of the endplates,
d) expanding the tube to force the rings to a second expanded locked state,
e) collapsing the expanded tube to leave behind the locked rings to support the disc space, and
f) removing the tube.

Also in accordance with the present invention, there is provided an intervertebral fusion device for supporting a disc space, comprising:
a) a substantially semicircular array of rings having a first unexpanded state and a second expanded, locked state, wherein each ring in its expanded, locked state has a diameter corresponding substantially to a height of the disc space.

Figure 3A:
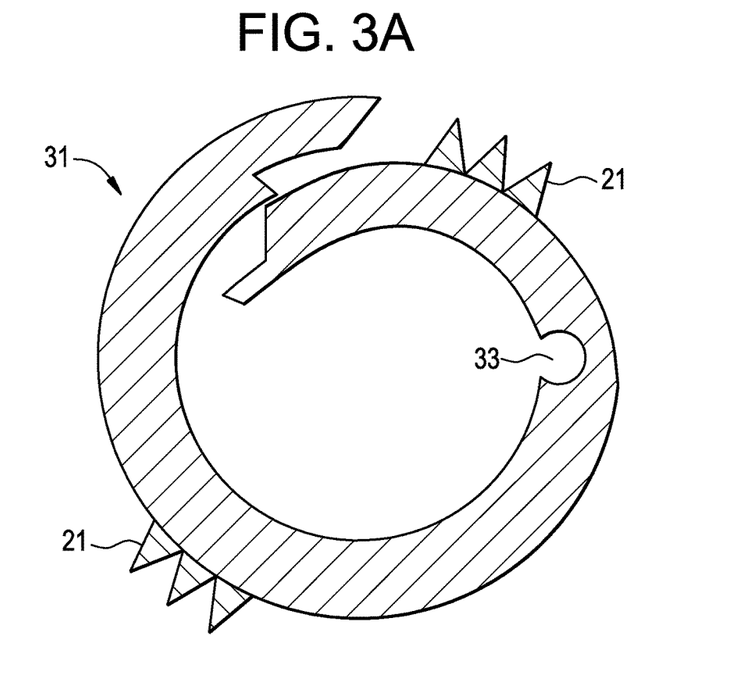
FIGS. 3a-3b show collapsed and expanded rings of the present invention having gripping teeth and a bend zone (or "living hinge").
Figure 3B:
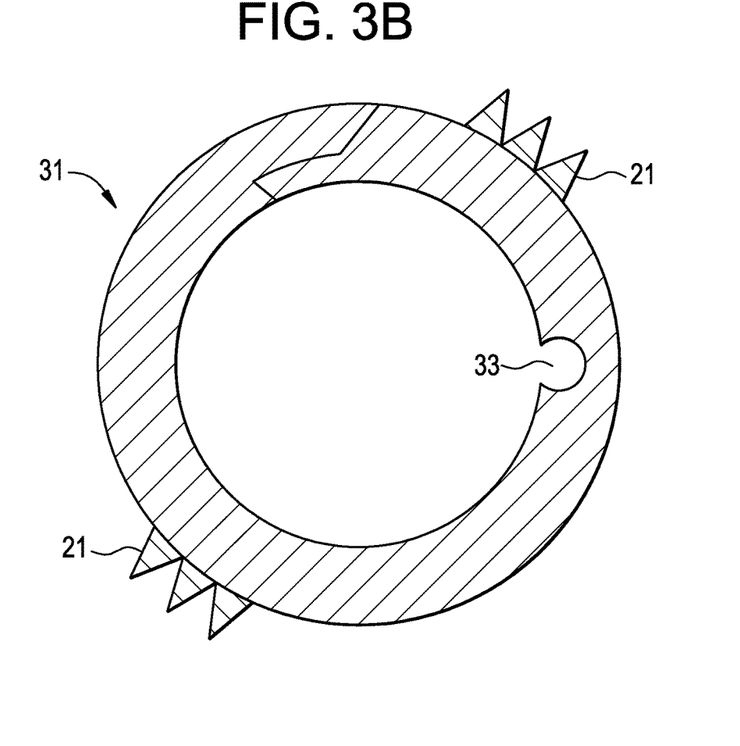

In some embodiments, and now referring to FIGS. 3a and 3b, the ring comprises sets of gripping teeth 21 that extend outward from the expanded ring. These gripping teeth are adapted for gripping the opposing endplates of the vertebral bodies adjacent the disc space. The ring 31 of these FIGS. 3a and 3b also posessess a bend zone 33 having reduced wall thickness that facilitates the expansion of the ring.

Figure 4A:
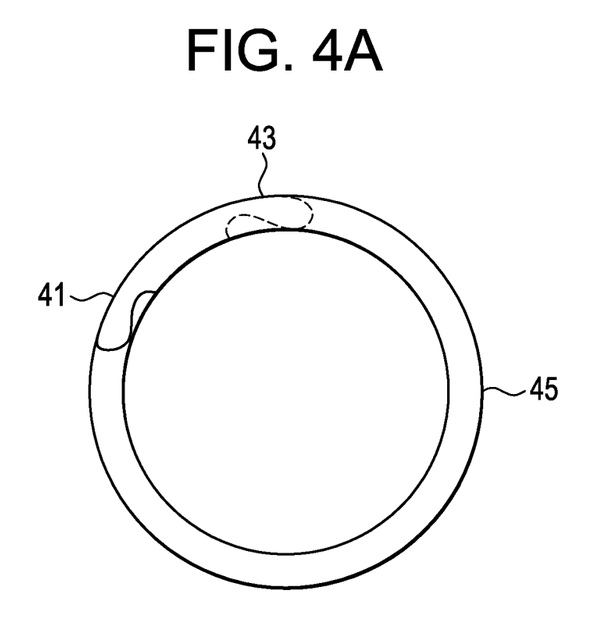
FIGS. 4a and 4b represent another embodiment of the present invention wherein the ends of the open collapsed ring are in a side-by-side relationship in the collapsed state.
Figure 4B:
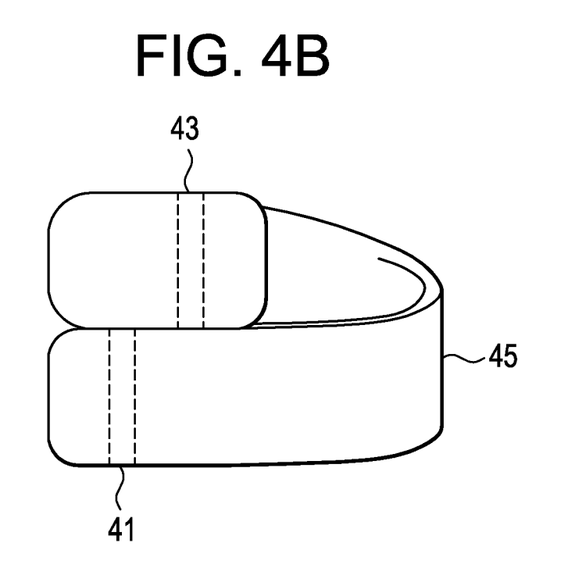
Figure 5A:
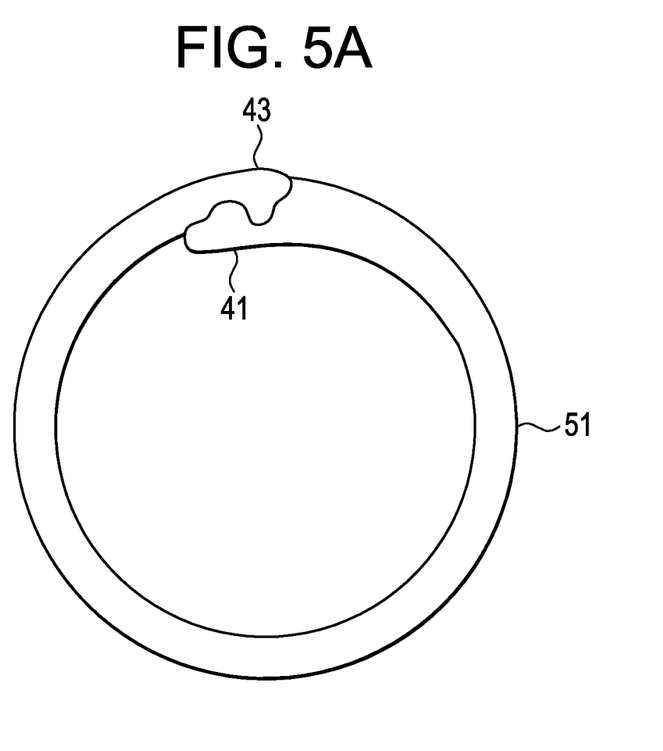
FIGS. 5a and 5b show the ring of FIGS. 4a and 4b in its expanded, locked state.
Figure 5B:
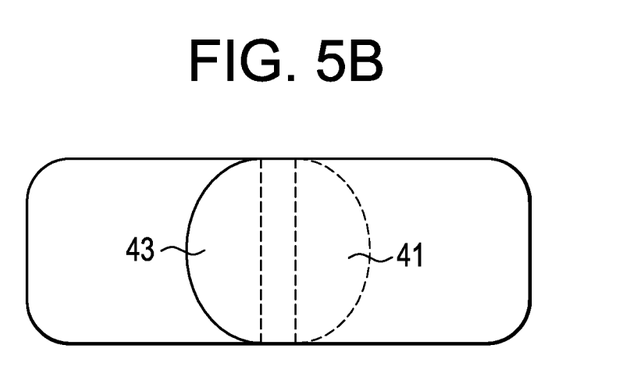

FIGS. 4a and 4b represent another embodiment of the present invention wherein the ends 41,43 of the open collapsed ring 45 are in a side-by-side relationship in the collapsed state. Now referring to FIGS. 5a and 5b, as the balloon (not shown) expands and ring 51 is distracted, the ring expands in diameter while the side-coiled member re-aligns its axis with that of the other member and the device locks when fully distracted.

Therefore, in accordance with the present invention, there is provided a method of making an in-situ formed intervertebral fusion cage, comprising the steps of:
a) inserting an assembly into a disc space, the assembly comprising an expandable balloon having a plurality of expandable rings thereon,
b) expanding the expandable balloon to expand the expandable rings.

Also in accordance with the present invention, there is provided a method of making an in-situ formed intervertebral fusion cage, comprising the steps of:
a) inserting into a disc space a fusion ring in an unexpanded state,
b) expanding the ring to an expanded state.

Also in accordance with the present invention, there is provided a method of making an in-situ formed intervertebral fusion cage, comprising the steps of:
a) inserting into a disc space a spiral-shaped fusion ring having an inner end and a outer end, wherein the ends overlap,
b) expanding the ring so that the first end abuts the second end.

The rings of the present invention could be continuous spiral coils that uncoil as they are distracted. The coils could have mechanical features that enable its shape to be fixed in space (crimp zones, interference fits, adhesives, keys, etc.). The coils could be nested. The nesting could be produced by deploying the first coil, sliding a second coil down the flexible tube and deploying that second coil, etc. The nested coils would exert progressively higher distraction strength. Theoretically, a predetermined interbody distraction load could be applied by concentric sequential deployment of spring coils. The coils could be made of a memory metal that deploys upon contact with the body's heat.

In some embodiments, each ring comprises chain links forming a linked chain. These links enable limited excursion but provide very high tensile strength once they are distracted. These chain links would require a fixation means—adhesives, crimps, keys, interference fits, stakes, etc.

In some embodiments, the expansion member (inner balloon) could be left in place to act as a delivery catheter for chemicals, energy, or diagnostic information as a quasi-chronic implant that is preferably removed before twenty eight days. In particular, the inner balloon may be adapted to deliver at least one of red or near infrared light, dissolved oxygen or nitric oxide, profound hypothermia, hyperthermia, electrical stimulation, mechanical stimulation, or growth factors.

Without wishing to be tied to a theory, it is believed that leaving a quasi-chronic catheter in the disc space to be fused is desirable because a significant amount of the bone graft placed in the disc space often necrotizes before vascularization and engraftment takes place, and the delivery catheter described above can alleviate some problems associated with ischemia and delayed engraftment.

Similarly, irradiation of the graft with red/NIR light might improve cell survival in the graft.

Likewise, since oxygen therapy has been shown to be beneficial in dermal wounds, catheter-based delivery of oxygen should be expected to improve the acute phase of hard tissue engraftment.

In some embodiments, mechanical energy is transferred through the catheter in order to drive bulk flow and thereby promote diffusion of metabolic products and wastes. One example of such mechanical energy is ultrasonic stimulation of graft tissues and bone remodeling.

In some embodiments, the expandable rings could comprise a part of an outer balloon or bladder that cures after hydraulic deployment. The outer bladder could allow the instrument-based flexible inner balloon (that expands the rings) to pass through it. Upon expansion, the implant-based outer bladder forms a soft ring of material surrounding the instrument-based flexible inner balloon that substantially conforms to the endplate geometry while preserving a near-ideal load-bearing circular void in the middle of the bladder. The outer bladder could cure on exposure to heat, light or well-timed chemical reaction. The instrument-based flexible inner balloon could be used to deliver the curing queue.

Now referring to FIGS. 6a-d, there is provided an embodiment of the present invention wherein curable bladders 65 are placed as spaced rings into the disc space as a fusion device. In this particular case, the device is placed in the L4-L5 disc space. In these embodiments, a "curable bladder ring" is an annular expandable device, such as a balloon, filled with a curable fluid component.

Preferably, the curable bladders of FIG. 6a-d are inserted into the disc space by carrying out the following procedure:
 a) placing a plurality of curable bladder rings 65 onto the inner balloon 61;
 b) inserting the bladder rings/inner balloon assembly into the disc space;
 c) expanding the inner balloon to expand and then compress the bladder rings;
 d) curing the bladder rings to produce a permanent, ringed, load-bearing implant; and
 e) (optionally) removing the inner balloon to produce a permanent implant consisting essentially of spaced rings.

In other embodiments, the plurality of curable bladder rings are inserted into the disc space prior to the insertion of the inner balloon into the disc space. In still other embodiments, the plurality of curable bladder rings are inserted into the disc space after the insertion of the inner balloon into the disc space.

Figure 6A:
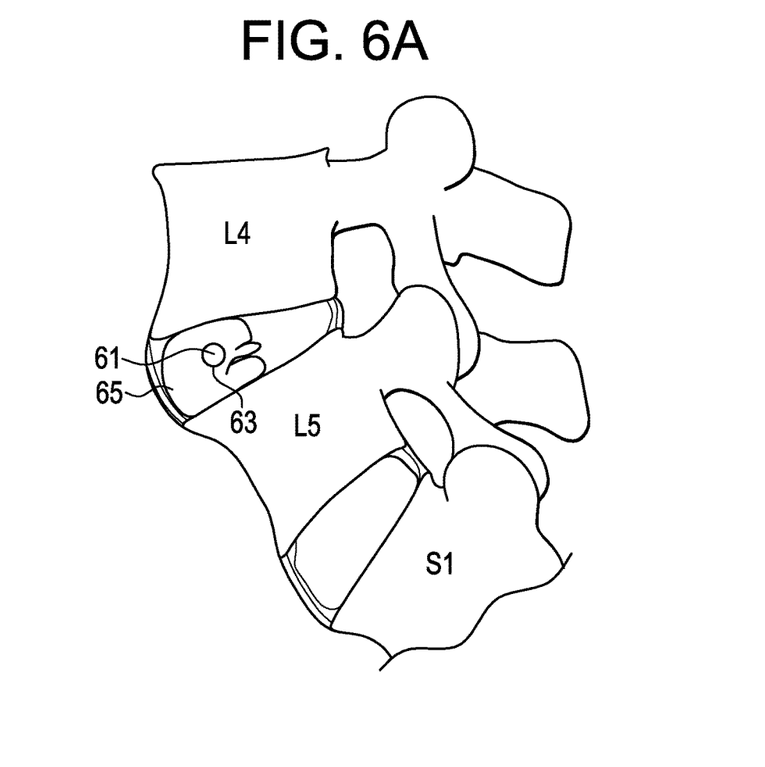
FIG. 6a discloses a device of the present invention positioned in the L4-L5 disc space.
Figure 6B:
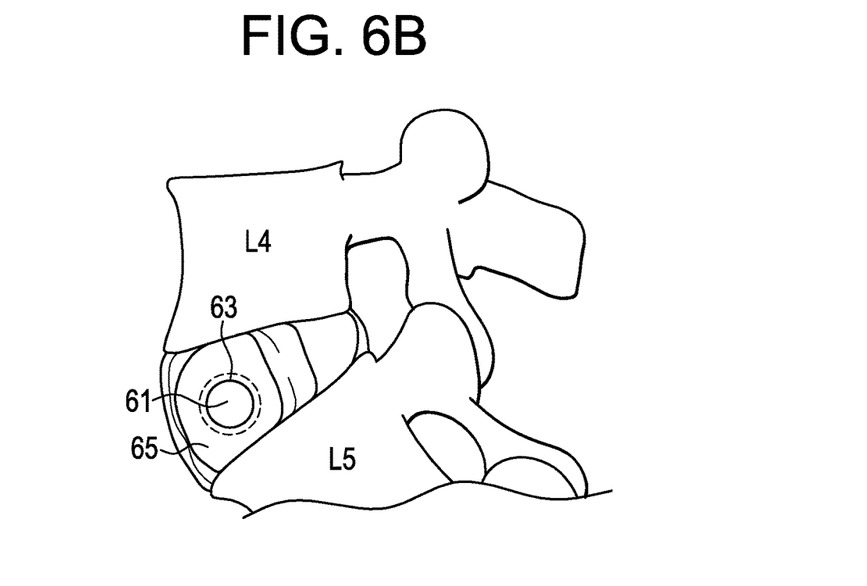
FIGS. 6b and 6c disclose side and axial views of a device of the present invention positioned in an anterior portion of the disc space.

Now referring to FIG. 6b, preferably, the fluid in the expanded bladder ring has a relatively low pressure, which allows it to conformally map to the local disc space geometry.

Figure 6C:
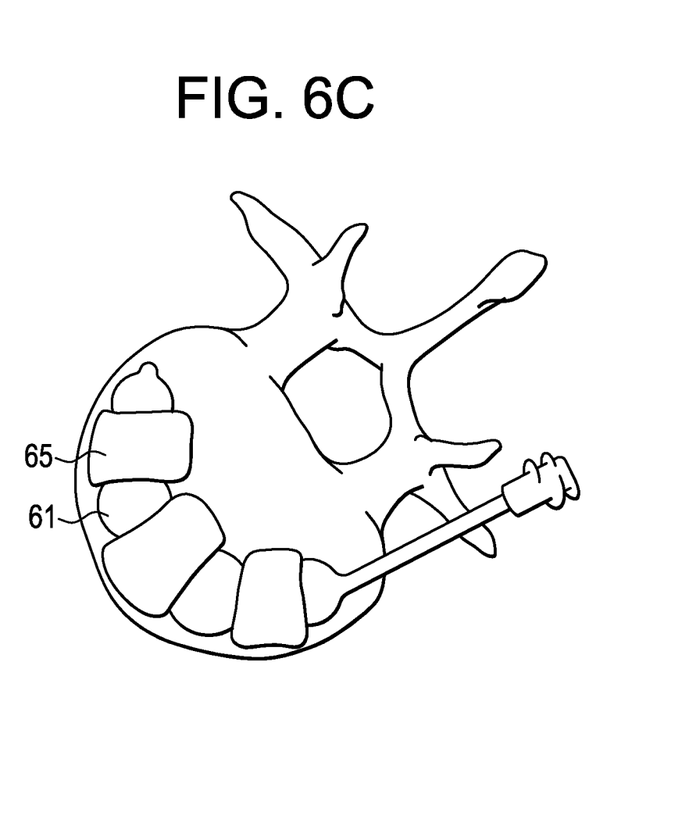
Figure 6D:
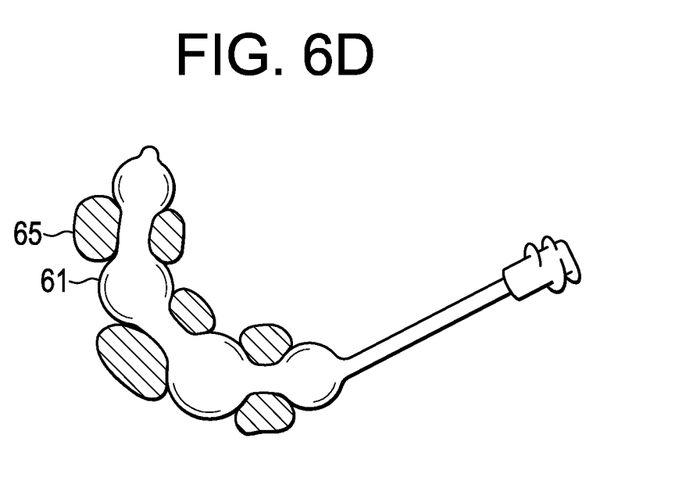
FIG. 6d discloses a device of the present invention in its expanded state.

Now referring to FIG. 6c, preferably, placement of the bladder rings is carried out upon the anterior rim of the disc space. In these embodiments, the fusion space is localized to the posterior aspect of the disc space. As the posterior aspect represents the shortest distance between the opposing endplates (as shown in FIG. 6b), this embodiment may reduce the distance over which neovascularization must occur, and thereby reduce necrosis.

In some embodiments, the inner balloon preferably comprises either PTFE or PET. When these materials are selected, this inner balloon can be made to have a very small outer dimension prior to expansion. In some embodiments, the bladder ring comprises either a fabric, ePTFE, or another plastic. More preferably, the bladder ring further has an osteo-integrating or high friction outer surface to assist in fusion or stabilization.

Therefore, in accordance with the present invention, there is provided an assembly for inserting an intervertebral fusion device, comprising:
 a) a first flexible tube 61 having an outer radius 63 and a throughbore, a first unexpanded state and a second expanded state,
 b) a plurality of bladder rings 65 having a first unexpanded state and a second expanded, locked state,
  wherein each bladder ring surrounds the outer radius of the tube and is filled with a curable component,
  wherein the plurality of rings are in their unexpanded states when the tube is initially in its unexpanded state, and
  wherein the plurality of bladder rings are in their expanded states once the tube has been placed in its expanded state.

Preferably, the first flexible tube has an arcuate expanded shape.

Now referring to FIGS. 7a-e, there is provided preferred embodiments of lockable rings of the present invention. In these figures, the "ring" comprises a top and bottom plate connected by a pair of movable struts. Expansion of the balloon (not shown) causes elongation of the struts. Generally, the struts contain mechanical features that prevent the expanded plates from collapsing back together. In the particular embodiment of FIGS. 7d-e, the mechanical feature is a ratchet and pawl mechanism 77 featuring one way teeth.

Therefore, in accordance with the present invention, there is provided an intervertebral fusion device comprising an assembly for inserting an intervertebral fusion device, comprising:
 a) a first flexible tube (not shown) having an outer radius and a throughbore, a first unexpanded state and a second expanded state,
 b) a plurality of expandable rings 71 having a first unexpanded state (FIG. 7a) and a second expanded, locked state (FIG. 7b), wherein each ring comprises;
  i) upper and lower plates 73, each plate having an outer surface 74 adapted for gripping a vertebral endplate and an inner surface 75 adapted for bearing against the outer radius of the first flexible tube, and
  ii) a pair of elongatable struts 76 connecting the upper and lower plates, each strut adapted to resist recession,
  wherein each expandable ring surrounds the outer radius of the tube,
  wherein the plurality of rings are in their unexpanded states when the tube is initially in its unexpanded state, and
  wherein the plurality of rings are in their expanded states once the tube has been placed in its expanded state.

Figure 7A:
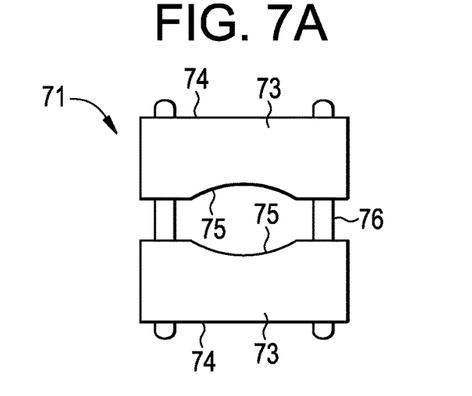
FIGS. 7a and 7b disclose side views of a collapsed and expanded ring of the present invention having expandable struts.
Figure 7B:
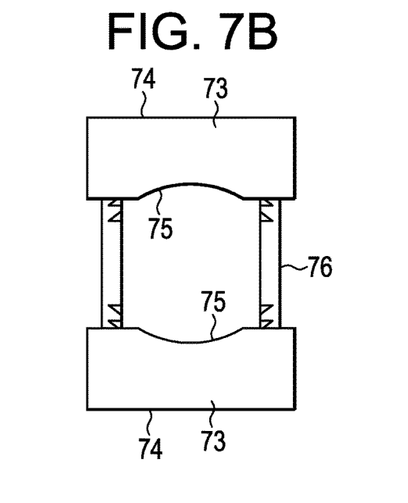
Figure 7C:
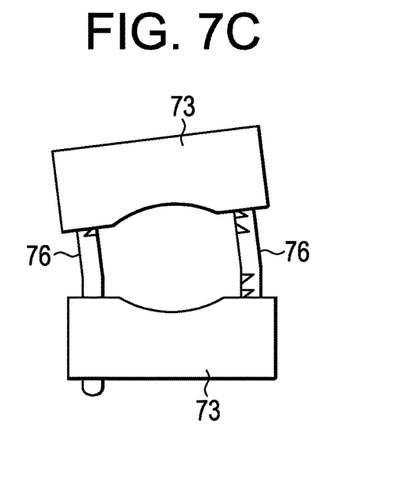
FIGS. 7c and 7d disclose cross-sections of a collapsed and expanded ring of the present invention having expandable struts.
Figure 7D:
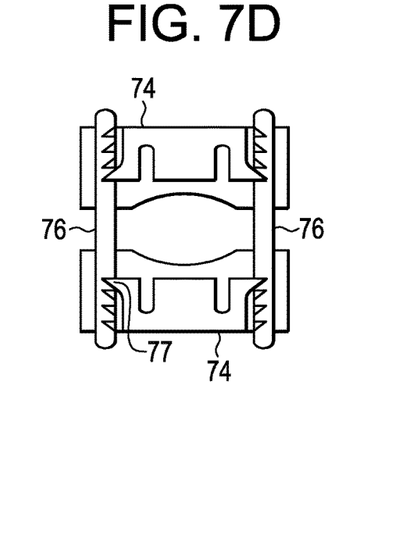
Figure 7E:
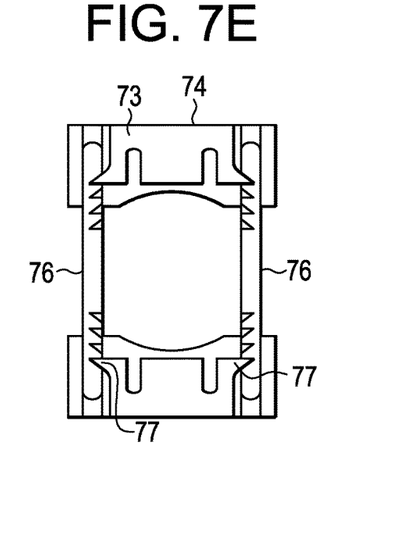
FIG. 7e shows a side view of a lordotic ring of the present invention

FIG. 7e Shows a Side View of a Lordotic Ring of the Present Invention

In some embodiments, the rings consist of multiple components connected by sliding keyways. Once distracted, the keyways could be fixed relative to one another by the various means described above. The keyway would replace the toothed irreversible fixation system described in FIGS. 1a and 1b above.

Now referring to FIGS. 8a-8i, there are provided embodiments of a device of the present invention containing keyways.

In particular, in accordance with the present invention, there is provided an intervertebral fusion device comprising:
a) first U-shaped component 81 having first 82 and second 83 legs and a curved intermediate region 84 comprising a convex surface 85 and a concave surface 86,
b) second U-shaped component 91 having first 92 and second 93 legs and a curved intermediate region 94 comprising a convex surface 95 and a concave surface 96,
wherein the concave surfaces oppose each other, and the convex surfaces are adapted for gripping respective opposing vertebral endplates, and
wherein the first legs of each component are adapted to nest with each other to form a first keyway, and
wherein the second legs of each component are adapted to nest with each other to form a second keyway.

Figure 8A:
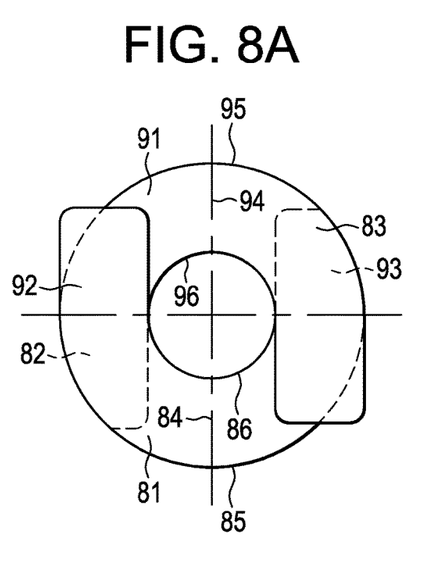
FIGS. 8a-b disclose front and side views of an unexpanded device of the present invention having a keyway.
Figure 8B:
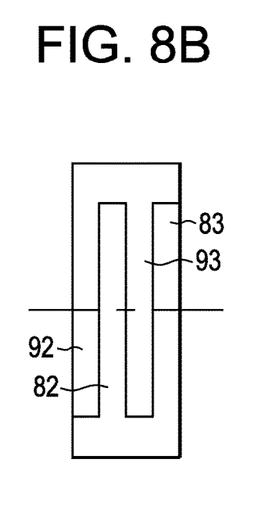
Figure 8C:
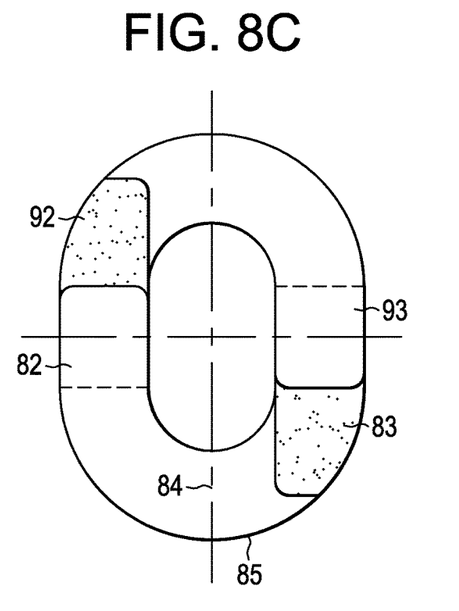
FIGS. 8c-d disclose front and side views of an expanded device of the present invention having a keyway.
Figure 8D:
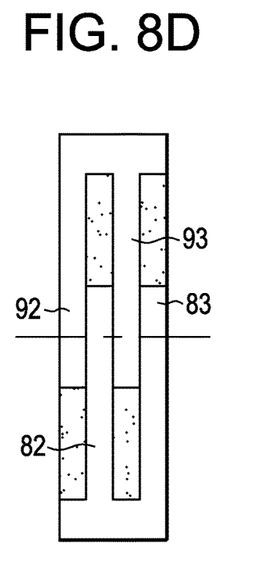
Figure 8E:
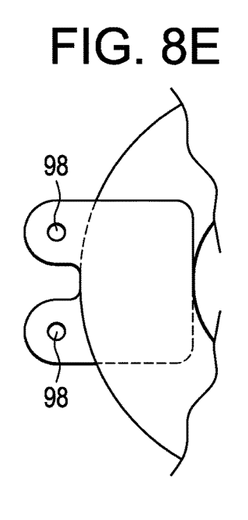
FIGS. 8e-g disclose front and side views of an device of the present invention having throughholes adapted for reception of a securement pin.
Figure 8F:
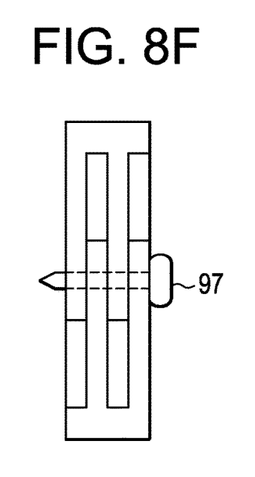
Figure 8G:
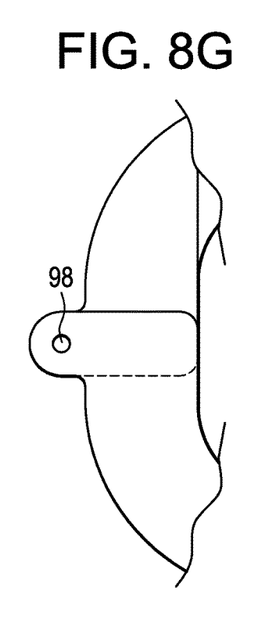

In some embodiments, and now referring to FIGS. 8e-g, the device further comprises a securement pin 97, and the first legs of each component further comprise a throughhole 98, wherein the securement pin passes through each throughhole.

Figure 8H:
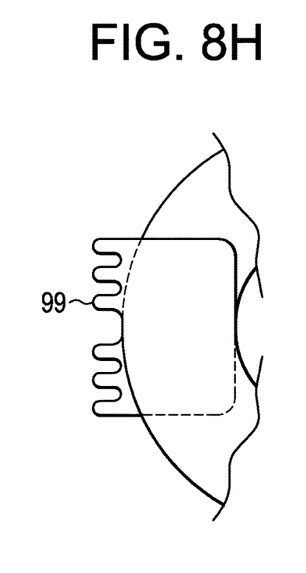
FIGS. 8h-i disclose a device of the present invention having ratchet teeth adapted for one way movement.
Figure 8I:
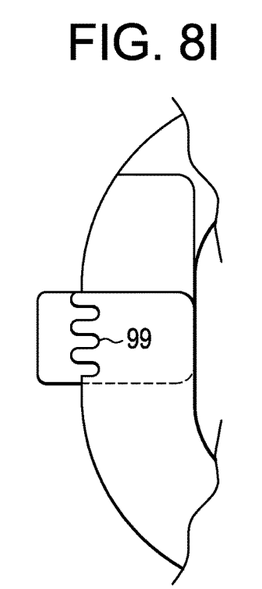

In some embodiments, and now referring to FIGS. 8h-i, the first legs of each component further comprise ratchet teeth 99 adapted for one way movement.

As shown, each leg comprises a pair of parallel plates that nest with the parallel plates of the opposing leg. Adhesives could be applied between the sliding plates of each leg. The ultimate bond would be primarily loaded in shear. The adhesive could contain particulate or fiber reinforcement to withstand the shear.

In some embodiments, the faces on each plate could be textured or contoured to support load bearing. One-way ratchet and pawl mechanisms could be placed on the faces of each plate to prevent the plate from sliding after deployment.

The ring geometry could be modified to a different shape or to accommodate mechanical keys to prevent collapse.

In one embodiment, a hardenable, resorbable, bone fusion-promoting composition is delivered into the disc space by first providing a resorbable, expandable balloon to the disc space, and then filling the balloon with the fusion-promoting composition.

Preferred resorbable, expandable balloons include inflatable bags, thin-walled balloons, and fabric jackets.

In some embodiments, a mesh balloon is selected. The mesh nature of the bags provides for enhanced osteogenic connection between the internal cavity and the patient's tissue.

In some embodiments, the balloons are perforated to provide osteogenic avenues between the bone fusion-promoting composition and the patient's tissue.

Preferably, the balloon is resorbable. When the balloon is resorbable, its eventual resorption after fusion has taken place eliminates problems associated with permanent implants. More preferably, the resorbable balloon is made from a resorbable polymers as discussed below. However, in other embodiments, the balloon may include non-resorbable components or be completely non-resorbable.

Compositions for filling the balloon of this invention are known in the art. Hardenable, resorbable compositions include setting ceramics, polymerizable monomers and polymers, polymers flowable at temperatures above body temperature, and polymers solubilized in a biocompatible solvent. Examples of resorbable setting ceramics include calcium phosphates, hydroxyapatites and calcium sulfates. Examples of polymerizable resorbable monomers and polymers include poly(propylene fumarate), polyoxaesters, polyurethanes and polyanhydrides. In one preferred embodiment, the hardenable composition is a photopolymerized polyanhydride. In this embodiment, irradiation can be used to control the polymerization process, therefore, a partially polymerized putty can be made, then hardened by continuing the polymerization with irradiation after the composition has been placed. Examples of resorbable polymers flowable at temperatures above body temperature include polymers and copolymers of lactic acid, glycolic acid, carbonate, dioxanone, and trimethylene carbonate. An example of a biocompatible solvent that can be used to solubilize the aforementioned polymers include dimethyl sulfoxide.

In order to improve the osteoconductivity of the aforementioned hardenable, resorbable compositions, they may be delivered to the site as an in-situ formed porous scaffold. Techniques of in situ forming porous scaffolds are known in the art and include porogen leaching and foaming with gas-producing elements.

In preferred embodiments of this invention, the hardenable, resorbable compositions incorporate an osteoinductive component. Osteoinductive components include growth factors such as bone morphogenetic proteins that can be grafted onto or mixed into said hardenable compositions. The term "growth factors" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; members of the insulin-like growth factor (IGF) family, including IGF-I and -II; the TGF-β superfamily, including TGF-β1, 2 and 3 (including MP-52); osteoid-inducing factor (OIF), angiogenin(s); endothelins; hepatocyte growth factor and keratinocyte growth factor; members of the bone morphogenetic proteins (BMP's) BMP-1, BMP-3; BMP-2; OP-1; BMP-2A, BMP-2B, and BMP-7, BMP-14; HBGF-1 and HBGF-2; growth differentiation factors (GDF's), members of the hedgehog family of proteins, including indian, sonic and desert hedgehog; ADMP-1; members of the interleukin (IL) family, including IL-1 thru IL-6; GDF-5 and members of the colony-stimulating factor (CSF) family, including CSF-1, G-CSF, and GM-CSF; and isoforms thereof.

In addition, bone-producing cells, such as mesenchymal stem cells (MSCs), can be delivered with the hardenable compositions by first encapsulating the cells in hydrogel spheres then mixing in.

MSCs provide a special advantage because it is believed that they can more readily survive relatively harsh environments; that they have a desirable level of plasticity; and that they have the ability to proliferate and differentiate into the desired cells.

In some embodiments, the mesenchymal stem cells are obtained from bone marrow, preferably autologous bone marrow. In others, the mesenchymal stem cells are obtained from adipose tissue, preferably autologous adipose tissue.

In some embodiments, the mesenchymal stem cells used in an unconcentrated form. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated by reference in its entirety, are preferably used. In some embodiments, the matrix used to filter and concentrate the MSCs is also administered into the container.

In another embodiment of the invention, the hardenable, resorbable, bone fusion-promoting composition is delivered to the disc space as a partially hardened, shapable putty. The putty can then be pressed into the disc space. Following shaping, the partially hardened composition will completely harden to provide a rigid fixation of the spine.

We claim:

1. An intervertebral fusion device for supporting a disc space, comprising:
   a) a substantially semicircular array of rings having a first unexpanded state and a second expanded, locked state, wherein each ring in its expanded, locked state has a diameter corresponding substantially to a height of the disc space,
   wherein each ring has an outer diameter, an inner diameter, and a thickness therebetween, and
   wherein each ring has first and second opposed sets of gripping teeth that extend outward from the expanded ring, wherein the gripping teeth are adapted for gripping opposing endplates of vertebral bodies adjacent the disc space,
   wherein the teeth point substantially perpendicularly to their respective rings in the plane of their respective ring.

2. The device of claim 1 wherein each ring has a first and second end, the first end having a first mating tooth, the second end having a second mating tooth, wherein the first and second mating teeth mate with each other in the expanded state to prevent movement of the ring to its unexpanded state.

3. The device of claim 1 wherein the plurality of rings are present in the form of a plurality of spiral coils.

4. The device of claim 3 wherein the plurality of spiral coils are nested.

5. The device of claim 3 wherein the plurality of spiral coils are made of a memory metal.

* * * * *